US011717639B2

(12) United States Patent
Baeuerle et al.

(10) Patent No.: US 11,717,639 B2
(45) Date of Patent: Aug. 8, 2023

(54) COMBINATORIAL THERAPEUTIC SYSTEMS AND METHODS (71) Applicant: Cognifisense, Inc., Sunnyvale, CA (US)

(72) Inventors: Tassilo Baeuerle, Sunnyvale, CA (US); Harald F. Stock, Sunnyvale, CA (US)

(73) Assignee: COGNIFISENSE, INC., Sunnyvale, CA (US)

( * ) Notice: Subject to any disclaimer, the term of this patent is extended or adjusted under 35 U.S.C. 154(b) by 180 days.

(21) Appl. No.: 16/965,203

(22) PCT Filed: Jan. 25, 2019

(86) PCT No.: PCT/US2019/015301
§ 371 (c)(1),
(2) Date: Jul. 27, 2020

(87) PCT Pub. No.: WO2019/148047
PCT Pub. Date: Aug. 1, 2019

(65) Prior Publication Data
US 2021/0060290 A1  Mar. 4, 2021

Related U.S. Application Data (60) Provisional application No. 62/654,945, filed on Apr. 9, 2018, provisional application No. 62/642,726, filed on
(Continued)

(51) Int. Cl.
*A61M 21/02* (2006.01)
*A61P 25/04* (2006.01)
(Continued)

(52) U.S. Cl.
CPC .......... *A61M 21/02* (2013.01); *A61K 31/137* (2013.01); *A61K 38/07* (2013.01); *A61P 25/04* (2018.01);
(Continued)

(58) Field of Classification Search
CPC .......... A61M 21/02; A61M 2021/0016; A61M 2021/0022; A61M 2021/0027;
(Continued)

(56) References Cited

U.S. PATENT DOCUMENTS 6,057,846 A * 5/2000 Sever, Jr. .............. A61M 21/00
345/419
6,186,145 B1 * 2/2001 Brown ................... A61B 5/168
600/300

(Continued)

FOREIGN PATENT DOCUMENTS

WO    WO2017087567    5/2017

OTHER PUBLICATIONS

International Search Report and Written Opinion issued in PCT/US2019/015301 dated Mar. 15, 2019.
(Continued)

*Primary Examiner* — Kaylee R Wilson
(74) *Attorney, Agent, or Firm* — Workman Nydegger (57) ABSTRACT

Combinatorial therapeutic systems can include an artificial sensory experience and a therapeutically effective amount of an analgesic selected from tapentadol or difelikefalin (CR845). Methods for treating and/or mitigating pain can include at least (i) receiving a therapeutic dose of an analgesic selected from tapentadol or difelikefalin (CR845) and (ii) receiving an artificial sensory experience. The artificial sensory experience can include one or more of 2D/3D/4D artificial sensory experiences, holography, augmented reality, virtual reality, and/or mixed reality. In some instances, the artificial sensory experience is virtual reality neuropsychological therapy or virtual reality distraction therapy.

20 Claims, 5 Drawing Sheets

Related U.S. Application Data on Mar. 14, 2018, provisional application No. 62/621,793, filed on Jan. 25, 2018.

(51) Int. Cl.
*A61K 31/137* (2006.01)
*A61K 38/07* (2006.01)
*A61M 21/00* (2006.01)

(52) U.S. Cl.
CPC ............ *A61M 2021/005* (2013.01); *A61M 2021/0016* (2013.01); *A61M 2021/0022* (2013.01); *A61M 2021/0027* (2013.01); *A61M 2021/0077* (2013.01); *A61M 2205/3553* (2013.01); *A61M 2205/507* (2013.01)

(58) Field of Classification Search
CPC .... A61M 2021/005; A61M 2021/0077; A61M 2205/3553; A61M 2205/3584; A61M 2205/507; A61M 2205/3375; A61M 2205/502; A61M 2205/581; A61M 2205/582; A61M 2205/583; A61M 2205/588; A61M 21/00; A61K 31/137; A61K 38/07; A61K 31/451; A61P 25/04

See application file for complete search history.

(56) References Cited

U.S. PATENT DOCUMENTS

| | | | |
|---|---|---|---|
| 6,425,764 B1 * | 7/2002 | Lamson | G16H 30/40 434/236 |
| 2008/0181876 A1 | 7/2008 | Johnson et al. | |
| 2010/0217619 A1 * | 8/2010 | Cox | G16H 80/00 715/757 |
| 2015/0248270 A1 * | 9/2015 | Lang | G16H 20/70 707/821 |
| 2018/0292888 A1 * | 10/2018 | Slepian | A61B 5/4836 |
| 2018/0296794 A1 * | 10/2018 | Clark | A61K 38/095 |

OTHER PUBLICATIONS

Albert-Vartanian A. et al, "Will peripherally restricted kappa-opioid receptor agonists (pKORAs) relieve pain with less opioid adverse effects and abuse potential?," Journal of Clinical Pharmacy and Therapeutics., vol. 41, No. 4, Jun. 1, 2016, pp. 371-382.

Hoffman Hunter G. et al., "The Analgesic Effects of Opioids and Immersive Virtual Reality Distraction: Evidence from Subjective and Functional Brain Imaging Assessments," Anesthesia and Analgesia., vol. 105, No. 6, Dec. 1, 2007, pp. 1776-1783.

Langford Richard M, "Is tapentadol different from classical opioids? A review of the evidence," British Journal of Pain, vol. 10, No. 4, Jul. 25, 2016, pp. 217-221.

McSherry Th Ere Sa et al, "Randomized, Crossover Study of Immersive Virtual Reality to Decrease Opioid Use During Painful Wound Care Procedures in Adults," Journal of Burn Care & Research, vol. 39, May 1, 2017, pp. 1-285.

* cited by examiner

COMBINATORIAL THERAPEUTIC SYSTEMS AND METHODS

BACKGROUND

Pain affects virtually all humans at some point in their lives. In particular, chronic pain is a major contributor to disability in the industrialized world and is the cause of an unquantifiable amount of suffering. However, chronic pain is more than a series of nociceptive or acute pain events. It is a complex condition consisting of physiological and psychological components. In fact, neuroimaging research has shown that chronic pain is associated with parts of the brain different from those associated with acute pain. Thus, to provide lasting relief from chronic pain, therapies should address both the physiological and the neuro-psychological components of chronic pain.

Commonly prescribed analgesics for pain include opioid analgesics, which are narcotic drugs that function in a manner similar to that of morphine. These agents work by binding to opioid and, in some cases, to noradrenaline receptors, which are found principally in the central nervous system and the gastrointestinal tract. "Opiates" are alkaloids derived from the opium poppy. "Opioids," a term often used synonymously with opiates, is frequently used to refer to the broader group of natural opium alkaloids and semi-synthetics derived from them. Research has shown that these centrally and/or peripherally acting opioids carry significant risk of side effects and/or addiction and have responder rates as low as 30%. Some opiates (e.g., tapentadol) show only marginal incremental pain reduction versus placebo. This means these pharmacological treatments offer limited effectiveness for a large proportion of chronic pain sufferers and carry significant risks. Moreover, these opioids, and most other analgesics, do not address the underlying; e.g., neuropsychological components of chronic pain; they simply mask the pain for a time.

The need for an effective (chronic) pain therapy to address both the physical and the psychological components of (chronic) pain speaks to a long-felt (but unmet) need for additional therapies. Needed therapies include those that not only treat and/or mitigate (chronic) pain, but also those that may reduce risk of opioid tolerance buildup, side effects, and addiction.

BRIEF SUMMARY

Embodiments described herein are directed to combinatorial therapeutic systems and methods for treating or mitigating pain. An exemplary combinatorial therapeutic system includes a centrally and/or peripherally acting analgesic and an artificial sensory experience. The analgesic can be any of an opioid, a serotonin-norepinephrine reuptake inhibitor (SNRI), or a neuropathic pain inhibitor. In one exemplary embodiment, the analgesic can be any of tapentadol, oxycodone, cepranopadol, difelikefalin (developmental code name CR845, Cara Therapeutics Kappa Opioid Receptor Agonist, aka KORA), and/or a combination of oxycodone and acetaminophen or a nonsteroidal anti-inflammatory drug (NSAID). Additionally, or alternatively, the analgesic can be the SNRT milnacipran. Additionally, or alternatively, the analgesic can be a neuropathic pain inhibitor, such as gabapentin or prebabalin. Any of the foregoing analgesic selections can be combined with an artificial sensory experience selected from 2D artificial sensory experience, 3D artificial sensory experience, 4D artificial sensory experience, holography, augmented reality, virtual reality, or mixed reality. In some embodiments, the virtual reality is virtual reality neuropsychological therapy (VRNT). In some embodiments, the virtual reality is virtual reality distraction therapy.

Methods for treating and/or mitigating pain include receiving an analgesic selected from an opioid, a serotonin-norepinephrine reuptake inhibitor, or a neuropathic pain inhibitor such as gabapentin or prebabalin and receiving an artificial sensory experience. The method act of receiving an analgesic can include receiving an opioid analgesic alone or in combination with acetaminophen or an NSAID. In a preferred embodiment, the opioid analgesic can include one or more of tapentadol, oxycodone, difelikefalin (CR845), and/or cepranopadol.

In some embodiments, receiving an analgesic can include receiving an SNRI, preferably milnacipran.

In some embodiments, receiving an analgesic can include receiving a neuropathic pain inhibitor. In some embodiments, receiving a neuropathic pain inhibitor includes receiving gabapentin or prebabalin.

Any of the foregoing method acts of receiving an analgesic can, in some embodiments, be combined in a combinatorial therapy with receiving an artificial sensory experience. Receiving the artificial sensory experience can include receiving one or more of 2D artificial sensory experience, 3D artificial sensory experience, 4D artificial sensory experience, holography, augmented reality, virtual reality, or mixed reality configured to visualize and/or virtually ameliorate the patient's pain, in some variations, according to the patient's own experience of that pain. In some variations, the artificial sensory experience is virtual reality, preferably VRNT or virtual reality distraction therapy.

Methods for treating and/or mitigating pain, particularly for treating and/or mitigating pain related to fibromyalgia, include receiving an SNRT, preferably milnacipran, or receiving a neuropathic pain medication, preferably gabapentin or pregabalin These methods can additionally include the method act of receiving an artificial sensory experience. The artificial sensory experience can be any of 2D artificial sensory experience, 3D artificial sensory experience, 4D artificial sensory experience, holography, augmented reality, virtual reality, or mixed reality. In some variations, the artificial sensory experience is virtual reality, preferably VRNT or virtual reality distraction therapy.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be apparent to one of ordinary skill in the art from the description or may be learned by the practice of the teachings herein. Features and advantages of embodiments described herein may be realized and obtained by means of the instruments and combinations particularly pointed out in the appended claims. Features of the embodiments described herein will become more fully apparent from the following description and appended claims.

BRIEF DESCRIPTION OF THE DRAWINGS

To further clarify the above and other features of the embodiments described herein, a more particular description will be rendered by reference to the appended drawings. It is appreciated that these drawings depict only examples of the embodiments described herein and are therefore not to be considered limiting of its scope. The embodiments will be described and explained with additional specificity and detail through the use of the accompanying drawings in which.

DETAILED DESCRIPTION

I. Introduction

Pain, and especially chronic pain, is a leading cause of morbidity, and analgesics such as opioids are prevalent in prescription regimens for managing pain. These opioids have responder rates of as little as 30%, and even novel analgesics like tapentadol have been reported as having limited efficacy beyond placebo. At the same time, particularly many opioid analgesics have serious potential side effects and may be addictive. This can lead to abuse. Moreover, regular administration of an opioid analgesic often leads to increased tolerance, reducing the efficacy of the treatment over time. Finally, these and many other analgesics act mostly to mask or temporarily diminish physiological aspects of the experience of pain but fail to address the important neuro-psychological components of pain. Consequently, there is a need for new system and methods for treating and/or mitigating pain.

As noted above, the embodiments described herein are generally directed to combinatorial therapeutic systems and methods for treating or mitigating pain. It has been surprisingly found that some analgesics, such as opioid analgesics and even some combinations of opioid with NSAID analgesics, as well as SNRIs, or neuropathic pain medications such as gabapentin or pregabalin, when combined with an artificial sensory experience, such as virtual reality, provide one or more benefits over the use of these analgesics or artificial sensory experiences alone. For example, the embodiments described herein are designed to overcome at least some of the limitations of prior pain treatment regimens by creating a method and/or system that is capable of treating and/or mitigating pain without sole reliance on analgesic therapies, and does so in a low cost, personalized, and repeatable way.

Embodiments described herein can additionally reduce the amount and/or frequency of opioid (and certain other) analgesics administered for pain management and may, in some instances, reduce the severity and/or frequency of severe acute pain or episodic/chronic pain. Additionally, or alternatively, aspects of the present disclosure may provide a synergistic benefit, increasing the efficacy and/or duration of the salubrious effects of opioid (and certain other) analgesics. Additionally, or alternatively, embodiments described herein may increase the efficacy of the artificial sensory experience, accelerate the pain reduction, extend the analgesic effect of the artificial sensory experience, and/or reduce the amount of training or use of the artificial sensory experience administered before analgesic effects are realized.

Further, prophylactic treatment regimens can be initiated to decrease the intensity of the pain and/or the duration of the pain, and in some instances, prophylactic treatment may eliminate any perception of pain or allow the patient to experience the pain with diminished (or without) negative psychological associations. Such embodiments can beneficially enable patients that experience chronic or persistent episodic pain to curb the perceived intensity and/or the duration of pain with less medication (i.e., in frequency and/or amount). Such implementations can measurably increase the patient's quality of life and reduce addiction and reliance on high levels of opioid medications, among other benefits.

II. Exemplary Combinatorial Treatment Systems

Figure 1:
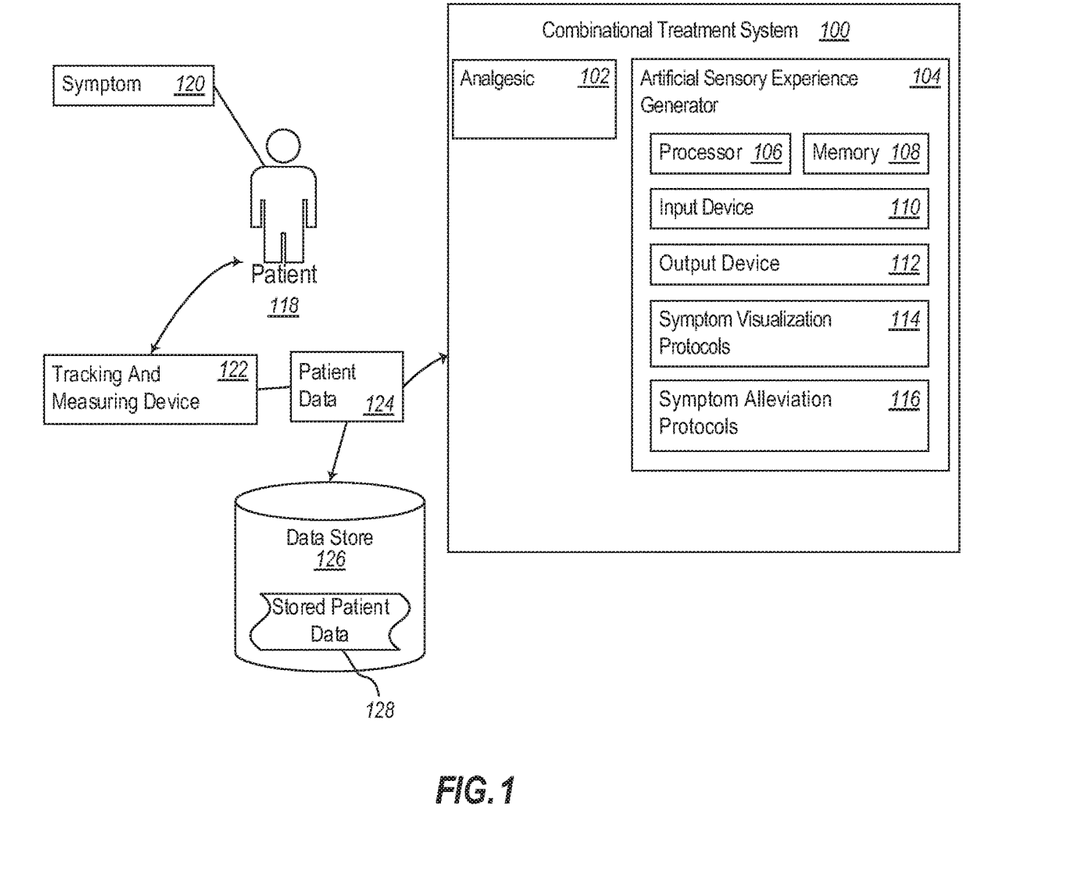
FIG. 1 is a schematic of an exemplary combinatorial therapeutic system that combines administration of an analgesic and an artificial sensory experience to a patient.

Referring now to FIG. 1, illustrated is an exemplary combinatorial therapeutic system 100 that combines administration of an analgesic and an artificial sensory experience to a patient. The combinatorial therapeutic system 100 includes an analgesic 102 and an artificial sensory experience generator 104.

The analgesic 102 can include a centrally- or peripherally-acting analgesic, preferably an opioid analgesic, more preferably any of tapentadol, oxycodone, cepranopadol, difelikefalin (CR845), and/or a combination of oxycodone and acetaminophen (commonly known as Percocet®). The analgesic 102 can be administered to a patient 118 in a combinatorial treatment method in dosage forms, frequencies, and concentrations that are at most equal to the approved and/or prescribed dosage for a given patient, as known in the art. However, in some embodiments, the analgesic 102 can be administered to the patient 118 in a combinatorial treatment method in frequencies and/or concentrations less than the patient's baseline or prescribed dosage prior to administration of the combinatorial treatment method.

A. Analgesics

As discussed herein, analgesics that can be used in the combinatorial therapeutic systems and methods described herein include opioids, SNRIs, as well as gabapentin or pregabalin, which can be used alone or in combination with acetaminophen or NSAIDs, such as ibuprofen or aspirin.

Preferred opioid analgesics include tapentadol, oxycodone, cepranopadol, and difelikefalin (CR845). Tapentadol is a centrally acting opioid analgesic of the benzenoid class with a dual mode of action as an agonist of the μ-opioid receptor and as a norepinephrine reuptake inhibitor. It has a potency somewhere between tramadol, another synthetic opioid, and morphine.

Oxycodone is a more powerful synthetic opioid similar in chemistry to natural opiates. Controlled release forms include OxyContin, OxyContin OTR, Xtampza ER, Targin, and Troxyca. Immediate release forms include OxyFast, OxyIR, OxyNorm, and Roxicodone. Oxycodone is often combined with a non-psychotropic analgesic. Examples include oxycodone with acetaminophen (Percocet, Endocet, Roxicet, and Tylox), oxycodone with aspirin (Percodan, Endodan, Roxiprin, and Oxycodan), and oxycodone with ibuprofen (Combunox).

Cepranopadol is a novel opioid analgesic of the benzenoid class and is currently under development internationally by Grünenthal, a German pharmaceutical company, and its partner Depomed, a pharmaceutical company in the United States, for the treatment of a variety of different acute and chronic pain states.

Difelikefalin (developmental code names CR845 and FE-202845) is an analgesic opioid peptide acting as a peripherally specific, highly selective agonist of the κ-opioid receptor (KOR). It is under development by Cara Therapeutics as an intravenous agent for the treatment of postoperative pain. An oral formulation has also been developed.

A preferred serotonin-norepinephrine reuptake inhibitor (SNRI) is milnacipran. Milnacipran is known to inhibit the reuptake of serotonin and norepinephrine in an approximately 1:3 ratio, respectively. It is presently understood that milnacipran exerts no significant actions on H1, α1, D1, D2, and mACh receptors, nor on benzodiazepine and opioid binding sites. In embodiments where the systems and methods described herein are implemented for the treatment or reduction of pain associated with fibromyalgia, milnacipran is the preferred analgesic.

In some embodiments, the analgesic includes medication used to treat neuropathic pain, preferably gabapentin or pregabalin. Gabapentin and pregabalin are both gabapentinoids—ligands of the auxiliary an subunit site of certain voltage-dependent calcium channels (VDCCs)—and each acts as an inhibitor of the an subunit-containing VDCCs. Gabapentin has been prescribed for use in treating neuropathic pain and may also be helpful in reducing opioid use following surgery, among other benefits. Pregabalin has been prescribed for use in treating neuropathic pain, epilepsy, fibromyalgia, and even some anxiety disorders.

Examples of other opioids that can be used for analgesia include morphine, codeine, and thebaine, which are found in opium poppies, hydrocodone (Vicodin, Norco, Lortab), hydromorphone, meperidine (Demerol), tramadol, fentanyl, oxymorphone, and the like.

Examples of other SNRIs that can be used for analgesia include desvenlafaxine (Pristiq), duloxetine (Cymbalta), venlafaxine (Effexor), and tramadol (a dual weak opioid and SNRI).

Although the present invention is primarily focused on combinatorial therapy involving patients suffering from chronic pain who are or might start using opioids and/or SRNIs prescribed for pain, with the desired result being the avoidance of addiction or abuse and/or a reduction in opioid usage, it will be appreciated that combinatorial therapy involving artificial sensory experience can also be used on subjects already addicted to opioids with the goal of reducing addiction and abuse, or on subjects with (severe) acute pain who are prescribed these analgesics in high doses or for extended periods of time.

Subjects that are addicted to opioids may not necessarily be "patients" in the strict sense of the word but might be doctor shopping or purchasing opioids from the street to support their drug habit, which may have begun innocently to treat pain but has itself become the problem. Opiate analgesics which are often abused by addicts include pharmaceuticals like oxycodone, fentanyl, codeine, morphine, hydrocodone, and the like, but they also include drugs (sometimes illegal) such as heroin, street versions or derivatives of fentanyl, alfentanil, remifentanil, sufentanil, carfentanil, dextropropoxyphene, methadone, etorphine, pethidine, levorphanol, and other benzylisoquinoline alkaloids. It is believed that combinatorial therapy can be useful to reduce usage, addiction, and abuse of opiates generally.

B. Artificial Sensory Experience

Any one or more of the foregoing analgesics 102 can be combined with an artificial sensory experience produced by the artificial sensory experience generator 104 to achieve at least some of the above-mentioned advantageous effects. The artificial sensory experience generator 104 can produce, for example, visual and/or other sensory stimuli to allow a patient 118 to virtually experience their symptom 120. As provided herein, the symptom 120 includes the multi-factorial experience of pain, although other symptoms are within the scope of this disclosure. In a preferred embodiment, the artificial sensory experience generator 104 enables the patient 118 to virtually experience aspects of the symptom 120 in accordance with the patient's own experience of the symptom 120. Stated another way, the artificial sensory experience generator 104 can be configured to reproduce one or more stimuli associated with a symptom 120 in a patient- and/or symptom-specific manner such that the artificial sensory experience is an accurate virtual representation of one or more aspects of the patient's symptom from the perspective of how the patient identifies with the virtually represented aspects of the symptom.

Aspects of the artificial sensory experience can be based on, for example, information received from the user via an input device 110. The user input can be incorporated into one or more of a symptom visualization protocol 114 or symptom alleviation protocol 116, which when processed by the processor 106 of the artificial sensory experience generator 104, causes the output device 112 to produce sensory stimuli representative of the symptom 120.

The principles described herein are not limited to the precise input or output devices, and the selection of input and output devices can depend on the nature of the artificial sensory experience administered to the patient. Nevertheless, exemplary input devices include microphones, touchscreens, motion tracking devices, projections, holograms, cameras, keyboards, stylus, mouse, or other pointer input, sensors of any type, and so forth. In a preferred embodiment, the input device includes a user interface for use in communicating information from/to a user. This includes, for example, a virtual control panel or similar.

The artificial sensory experience enabled by computing systems disclosed herein can include single or multi-sensory feedback and can be implemented by any number and/or type of output device associated with the computing system. For example, visual stimulus/feedback can be provided through a display, tactile feedback can be provided through a wearable housing a haptic element (e.g., haptic clothing like a haptic vest, haptic suit, and/or haptic gloves or a handheld device having a resonant actuator or the like), auditory feedback can be provided through speakers (e.g., standalone speakers, headphones, etc.), olfactory feedback can be provided by an olfactory feedback apparatus as known in the art or by a pre-selected set of defined scents or aromas, and gustatory feedback can be enabled by intra-oral devices known in the art and/or a pre-selected set of defined taste substances (e.g., spices, confections, chemicals, etc.).

As used herein, the term "displays" is meant to include devices that provide visual stimuli in the form of images, video, projections, holograms, or the like. Accordingly, a display can include a monitor or screen configured to produce images and/or video. A display can additionally include projectors configured to project images or video onto a surface and those configured for holography. A display can additionally include headsets or eyewear configured for virtual reality, augmented reality, and/or mixed reality.

The artificial sensory experience can, in some embodiments, mimic the patient's current pain level, or in some embodiments, the artificial sensory experience can mimic or represent a desired pain level, such that the effect of an opioid analgesic is synergistically enhanced, and/or a lower dose of the opioid analgesic can be administered with the same perceived therapeutic effect. In some embodiments, the artificial sensory experience can mimic the patient's current pain experience and then change the experience to represent the same pain as a neutral (e.g., an absence of pain) or even a pleasant experience. In some embodiments, the artificial sensory experience includes a combination of tactile, auditory, visual, olfactory, and/or gustatory feedback. For example, augmented reality can provide auditory and visual feedback at a smart phone that augments a portion of the patient's body—the portion experiencing pain, for example—to illustrate the patient's pain at the same level or a desired level of pain. This can help the user to visualize and hear the pain in a way similar to how the user experiences the pain, and by doing so, begin to control the intensity and/or duration of the pain. In some examples this effect may be further enhanced by providing visual, auditory, tactile or other stimuli, such as blurriness of vision or tingling, the user might experience if they actually used more analgesic. The analgesic taken therewith can have increased efficacy as a result of the augmented reality feedback.

In some embodiments, the output device 112 can provide a virtual representation of the symptom 120 in any of a 2D/3D/4D digital system. It should be appreciated that the foregoing dimensionality of the digital systems is made with respect to a user's perspective of the digital system. For example, a 2D digital system can include visual representations provided on a flat display, such as a laptop or desktop monitor, the screen of a mobile electronic device, or similar.

These multi-dimensional digital systems can be coupled with other devices producing sensory stimuli (e.g., auditory stimulus provided by speakers, tactile stimulus provided by haptic clothing or devices, gustatory stimulus provided by intra-oral devices, and olfactory stimulus supplied by olfactory feedback apparatuses) to increase the dimensionality of the user experience. For example, the dimensionality of the aforementioned 2D digital systems can be increased by the addition of another visual dimension or by the addition of another sensory stimulus. With respect to the running example of a 2D digital system providing visual representations on a flat display, the dimensionality of the digital system can be increased to a 3D digital system through the incorporation of an additional visual dimension. For example, providing the visual representations in an immersive virtual reality experience provides three-dimensional visual stimulus to the user. As such, most virtual reality systems are at least 3D digital systems. It should be appreciated that some augmented reality and mixed reality implementations can also be considered 3D digital systems.

In some embodiments, a 3D digital system can include a 2D visual display having one or more additional, non-visual stimuli associated therewith. For example, a 3D digital system can be created by combining a 2D visual display implemented on a mobile electronic device with auditory stimulus provided by speakers associated with the mobile electronic device. The 2D visual display provides the first two dimensions of the eventual 3D digital system with the third dimension being provided by the additional sensory stimulus—the auditory stimulus provided by the speakers. Similarly, the addition of tactile, olfactory, or gustatory stimuli in place of the auditory stimulus would also create a 3D digital system.

Of note, as the dimensionality of artificial sensory experiences is defined herein, the type of visual stimulus forms the foundation of the dimensionality: a visual stimulus like that observed on the screen of a mobile electronic device is a 2D visual stimulus whereas a visual stimulus like that of an immersive virtual reality environment is a 3D visual stimulus. An additional dimension can be added to the dimensionality of 2D or 3D visual stimuli to create a 3D or 4D artificial sensory experience. For example, a 2D visual stimulus can become a 3D artificial sensory experience by including an additional sensory stimulus, such as a tactile, aural, olfactory, or gustatory stimulus. In a similar fashion, a 3D visual display (e.g., virtual reality) can become a 4D artificial sensory experience through the layering of a non-visual sensory stimulus, such as an auditory stimulus provided by speakers, a tactile stimulus provided by haptic clothing or devices, a gustatory stimulus provided by intra-oral devices, and an olfactory stimulus supplied by olfactory feedback apparatuses.

However, the layering of additional different stimuli may not increase the dimensionality of the system. That is, a 3D artificial sensory experience made of a 2D visual stimulus and a tactile stimulus, for example, does not become a 4D artificial sensory experience with the addition of another sensory stimulus, and a 4D artificial sensory experience made of a 3D visual stimulus and a tactile stimulus, does not become a 5D artificial sensory experience with the addition of another sensory stimulus. Further illustrating this point, while the addition of a first additional stimulus—such as an auditory stimulus—to a 2D visual display would create a 3D artificial sensory experience, layering additional different stimuli in addition to the auditory stimulus and 2D visual display would still result in a 3D artificial sensory experience, as those terms are used herein.

With continued reference to FIG. 1, the artificial sensory experience generator 104 is configured to provide a sensory experience to a user. These artificial sensory experience generators and associated artificial sensory experiences can be implemented using any of an array of computer systems, which are now increasingly taking a wide variety of forms. "Artificial sensory experience generators," as that term is used herein, include any computer system, device, or combination thereof that includes at least one processor and a physical and tangible computer-readable memory capable of having thereon computer-executable instructions that are executable by the processor. The breadth and operability of computer systems is discussed in greater detail below.

In short, computer systems can include a variety of devices, such as mobile phones, electronic appliances, laptop computers, tablet computers, wearable electronic devices, desktop computers, mainframes, and the like. As used in this disclosure, although not limited in this way, computer systems store and operate artificial sensory experience generators to enable the visualization and virtual alleviation of a patient's symptom (i.e., pain) as part of the combinatorial treatment systems disclosed herein and can be operably linked to various input and output devices. A computing system may be distributed over a network environment and may include multiple constituent computing systems (e.g., a cloud computing environment). In a cloud computing environment, program modules may be located in both local and remote memory storage devices.

In one embodiment, the artificial sensory experience is virtual reality as applied in virtual reality distraction therapy. In a preferred embodiment, the artificial sensory experience is virtual reality, more preferably virtual reality neuropsychological therapy. As used herein, the term "virtual reality neuropsychological therapy" or "VRNT" includes virtual reality systems for symptom management (e.g., pain management) that provide a patient with a virtual, yet realistic and strongly impactful, representation of the patient's symptoms (e.g., pain) and potentially even their alleviation, as disclosed in PCT Application No. PCT/US2016/062348, which is incorporated herein by reference (which uses the term "virtual reality neuro-therapy").

In another preferred embodiment, the artificial sensory experience is virtual reality distraction therapy. Virtual reality distraction therapy, sometimes also referred to as Virtual Reality relaxation therapy, utilizes a virtual reality environment to provide a therapeutic degree of relaxation and/or escapism. It can affect its therapeutic benefit by relaxing the patient and/or commanding the patient's focus away from the symptom (e.g., pain) to refocus the patient on a task such as collecting coins or shooting zombies in a video game simulated in the virtual environment. Research has shown that the capacity of humans to focus or pay attention is limited. An individual's focus or concentration on a symptomatic experience (e.g., pain) allows them to perceive the pain to a certain extent. Accordingly, perception of a symptomatic experience such as pain decreases when the individual's attention is distracted away from the stimulus, or more precisely, refocused on another task which provides high cognitive load.

While many of the results and discussion provided herein are directed to combinatorial therapies using VRNT and opioid analgesics, it should be appreciated that virtual reality distraction therapy in combination with opioid analgesics is also expected to have unexpected combinatorial and/or synergistic benefits. More particularly, combinatorial therapies that include virtual reality distraction therapy and any of the one or more analgesics disclosed herein can have an unexpected synergistic therapeutic effect beyond that which could be achieved using either alone.

Further, in some embodiments, combinatorial treatment systems and methods can include a systematic combination of VRNT and virtual reality distraction therapy with opioid analgesics to provide the beneficial effects disclosed herein. For example, virtual reality distraction therapy can be used during heightened symptomatic periods in combination with opioid analgesics to synergistically provide a therapeutic benefit to the patient, and VRNT can be used subsequently to assist the patient in reducing their reliance on the opioid analgesic and/or to make the opioid analgesic more effective at the same or lower concentrations. Other combinations of VRNT and virtual reality distraction therapy are also considered within the scope of this disclosure.

In some instances, a user's psychological state prevents the opioid analgesic from working to its full efficacy. By coupling the opioid analgesic with the artificial sensory experience, the user may be able to enter or change their psychological state that allows the opioid to reach its full potency and/or increase its effectiveness beyond (e.g., in duration or strength) its historic utility with the given patient.

In a preferred embodiment, the artificial sensory experience is virtual reality. The patient can be immersed within the virtual reality using, for example, a head mounted display or other headgear (for visual feedback), headphones (for auditory feedback), and paddles or controllers (which may include haptic elements for tactile feedback systems). The virtual reality environment can, for example, instruct the user to accomplish a task. The task may include a meditative session to calm and/or relax the individual, a meditative session to visualize the isolation and/or elimination of the pain, drawing and/or visualizing the pain (as in VRNT) to illustrate the pain as it would visually appear in location, color, intensity, and description (e.g., aching, pulsing, throbbing, stabbing, shooting, cramping, gnawing, burning, etc.) on an avatar representative of the patient. The pain may further be associated with sounds, smells, and/or tactile feedback that help the patient become immersed in a visual representation of the pain. The computer system and/or the user can then interact with the visualized pain and/or visualize its dampening, control, elimination, or the turning of the pain into a neutral or positive experience. In some embodiments, as the opioid analgesic takes effect (or as it is enabled to affect), a positive feedback loop is generated where the user's visualization of the pain decreases and the physiologic response of the opioid analgesic decreases pain in the patient.

III. Computer Systems of the Present Disclosure

As provided above, artificial sensory experience generators can include computer systems. In some embodiments, these computer systems are configured to, for example, execute symptom visualization and/or alleviation protocols, receive input from a user, and output various stimuli to the user. It will be appreciated that computer systems are increasingly taking a wide variety of forms. In this description and in the claims, the term "computer system" or "computing system" is defined broadly as including any device or system—or combination thereof—that includes at least one physical and tangible processor and a physical and tangible memory capable of having thereon computer-executable instructions that may be executed by a processor. By way of example, not limitation, the term "computer system" or "computing system," as used herein is intended to include personal computers, desktop computers, laptop computers, tablets, mobile electronic devices (e.g., smart phones and tablets), microprocessor-based or programmable consumer electronics, minicomputers, mainframe computers, multi-processor systems, network PCs, distributed computing systems, datacenters, message processors, routers, switches, and even devices that conventionally have not been considered a computing system, such as standalone mobile virtual reality headsets or wearables (e.g., glasses, smart watches, personal health monitors).

Within a computing system, the associated memory may take any form and may depend on the nature and form of the computing system. The memory can be physical system memory, which includes volatile memory, non-volatile memory, or some combination of the two. The term "memory" may also be used herein to refer to non-volatile mass storage such as physical storage media.

The computing system also has thereon multiple structures often referred to as an "executable component." For instance, the memory of a computing system can include an executable component. The term "executable component" is the name for a structure that is well understood to one of ordinary skill in the art in the field of computing as being a structure that can be software, hardware, or a combination thereof.

For instance, when implemented in software, one of ordinary skill in the art would understand that the structure of an executable component may include software objects, routines, methods, and so forth, that may be executed by one or more processors on the computing system, whether such an executable component exists in the heap of a computing system, or whether the executable component exists on computer-readable storage media. The structure of the executable component exists on a computer-readable medium in such a form that it is operable, when executed by one or more processors of the computing system, to cause the computing system to perform one or more functions, such as the functions and methods described herein. As a non-limiting example germane to the present application, an "executable component" can include computer-executable instructions for instantiating an artificial sensory experience. Such a structure may be computer-readable directly by a processor—as is the case if the executable component were binary. Alternatively, the structure may be structured to be interpretable and/or compiled—whether in a single stage or in multiple stages—so as to generate such binary that is directly interpretable by a processor.

The term "executable component" is also well understood by one of ordinary skill as including structures that are implemented exclusively or near-exclusively in hardware logic components, such as within a field programmable gate array (FPGA), an application specific integrated circuit (ASIC), Program-specific Standard Products (ASSPs), System-on-a-chip systems (SOCs), Complex Programmable Logic Devices (CPLDs), or any other specialized circuit. Accordingly, the term "executable component" is a term for a structure that is well understood by those of ordinary skill in the art of computing, whether implemented in software, hardware, or a combination thereof.

The terms "component," "service," "engine," "module," "control," "generator," or the like may also be used in this description. As used in this description and in this case, these terms—whether expressed with or without a modifying clause—are also intended to be synonymous with the term "executable component" and thus also have a structure that is well understood by those of ordinary skill in the art of computing. As a non-limiting example, the artificial sensory experience generators disclosed herein can include symptom visualization and alleviation protocols stored within memory (e.g., non-volatile memory) as computer-executable instructions that, when executed by the one or more processors (e.g., hardware processors) of the artificial sensory experience generator, cause the computer system that is (or includes) the artificial sensory experience generator to execute an artificial sensory experience, such as VRNT or virtual reality distraction therapy.

Accordingly, embodiments described herein may comprise or utilize a special purpose or general-purpose computing system. Embodiments described herein also include physical and other computer-readable media for carrying or storing computer-executable instructions and/or data structures. Such computer-readable media can be any available media that can be accessed by a general purpose or special purpose computing system. Computer-readable media that store computer-executable instructions are physical storage media. Computer-readable media that carry computer-executable instructions are transmission media. Thus, by way of example—not limitation—embodiments disclosed or envisioned herein can comprise at least two distinctly different kinds of computer-readable media: storage media and transmission media.

Computer-readable storage media include RAM, ROM, EEPROM, solid state drives ("SSDs"), flash memory, phase-change memory ("PCM"), CD-ROM or other optical disk storage, magnetic disk storage or other magnetic storage devices, or any other physical and tangible storage medium that can be used to store desired program code in the form of computer-executable instructions or data structures and that can be accessed and executed by a general purpose or special purpose computing system to implement the disclosed functionality of the invention. For example, computer-executable instructions may be embodied on one or more computer-readable storage media to form a computer program product.

Transmission media can include a network and/or data links that can be used to carry desired program code in the form of computer-executable instructions or data structures and that can be accessed and executed by a general purpose or special purpose computing system. Combinations of the above should also be included within the scope of computer-readable media.

Further, upon reaching various computing system components, program code in the form of computer-executable instructions or data structures can be transferred automatically from transmission media to storage media (or vice versa). For example, computer-executable instructions or data structures received over a network or data link can be buffered in RAM within a network interface module (e.g., a "NIC") and then eventually transferred to computing system RAM and/or to less volatile storage media at a computing system. Thus, it should be understood that storage media can be included in computing system components that also—or even primarily—utilize transmission media.

Those skilled in the art will further appreciate that a computing system (e.g., an artificial sensory experience generator that is or includes a computing system) may also contain communication channels that allow the computing system to communicate with other computing systems over, for example, a network. Accordingly, the methods described herein may be practiced in network computing environments with many types of computing systems and computing system configurations. The disclosed methods may also be practiced in distributed system environments where local and/or remote computing systems, which are linked through a network (either by hardwired data links, wireless data links, or by a combination of hardwired and wireless data links), both perform tasks. In a distributed system environment, the processing, memory, and/or storage capability may be distributed as well.

As a non-limiting example, symptom visualization protocols described herein may be stored on a network server where they are accessed and executed in real time by an end-user device, such as a smart phone or network connected smart display (e.g., XR glasses). Additionally, or alternatively, end-user data can be transmitted to a network server, and symptom visualization protocols can be updated based on the received end-user data to more accurately reflect the user's experience. In some embodiments, this may be a computationally intensive process, and by processing these data over a system of network-connected computing systems, the overall processing time can be significantly reduced while simultaneously reducing local processing demands on the visualization-protocol-hosting server.

Those skilled in the art will also appreciate that the disclosed methods may be practiced in a cloud computing environment. Cloud computing environments may be distributed, although this is not required. When distributed, cloud computing environments may be distributed internationally within an organization and/or have components possessed across multiple organizations. In this description and the following claims, "cloud computing" is defined as a model for enabling on-demand network access to a shared pool of configurable computing resources (e.g., networks, servers, storage, applications, and services). The definition of "cloud computing" is not limited to any of the other numerous advantages that can be obtained from such a model when properly deployed.

A cloud-computing model can be composed of various characteristics, such as on-demand self-service, broad network access, resource pooling, rapid elasticity, measured service, and so forth. A cloud-computing model may also come in the form of various service models such as, for example, Software as a Service ("SaaS"), Platform as a Service ("PaaS"), and Infrastructure as a Service ("IaaS"). The cloud-computing model may also be deployed using different deployment models such as private cloud, community cloud, public cloud, hybrid cloud, and so forth.

Although the subject matter described herein is provided in language specific to structural features and/or methodological acts, it is to be understood that the subject matter defined in the appended claims is not necessarily limited to the described features or acts so described. Rather, the described features and acts are disclosed as example forms of implementing the claims.

IV. Examples

The following examples illustrate how combinatorial therapy involving administration of analgesic coupled with artificial sensory experiences to patients with (chronic) pain can greatly improve one or more favorable outcomes. While the examples are hypothetical in nature, they are based on qualitative observations involving VRNT administered to and received by patients on the one hand, and analgesia administered to and taken by patients on the other. Based on extrapolations of such data, the inventors have concluded that combinatorial therapy involving administration of VRNT and analgesia will provide synergistic effects and unexpectedly favorable outcomes in several areas.

Artificial sensory experience (e.g., VRNT) and analgesia have fundamentally different modes of action. VRNT and other artificial sensory experiences are sensory and psychological in nature, with the patient receiving primarily visual stimulation and secondarily/optionally auditory, tactile, olfactory, or gustatory stimulation. These are believed to affect the patient's conscious and/or subconscious understanding and interpretation of pain; however, they are not known to directly affect biological causes of "pain" (or danger) signals from the body (signals from the nervous system which the brain interprets as pain)—such as injury, tissue damage, nerve damage or disease—or the nerves (nociceptor neurons) that respond to damaging or potentially damaging stimuli and transmit these signals via the spine to the brain (where the signals are interpreted as pain or something else).

Analgesics including opioids, SNRIs, SSRIs, gabapentin, and pregabalin are primarily physiological and biochemical in nature by blocking or interfering with transmission of pain impulses. They are secondarily psychological in the sense that they provide temporary relief of pain, which is positive and beneficial psychological experience. However, they can have serious negative psychological effects, such as minor or major intoxication and, worse, long-term addiction and withdrawal if reduced or curtailed.

It has now been found, or postulated, that combining the primarily psychological effects of artificial sensory experience, such as VRNT, with the primarily physiological effects of analgesics can synergistically reinforce each other and yield unexpectedly beneficial and favorable outcomes. In some cases, VRNT or other artificial sensory experiences can substantially increase the physiological and psychological efficacy of analgesics in reducing pain. In other cases, analgesics can substantially increase the psychological and physiological efficacy of VRNT or other artificial sensory experiences in reducing the perception of pain and better understanding the nature of pain, such as making pain more benign or controllable in the mind of the patient.

Favorable outcomes that can be provided by combinatorial therapy as disclosed herein include improved efficacy of analgesics as measured by one or more of: (1) an increase in the number of patients responding favorably to analgesic or responding to a greater extent to treatment; (2) a reduction in the amount of time required for analgesic to take effect; (3) a reduction in the dosage or amount of analgesic required for a given reduction in pain; (4) a reduction in the frequency of administration of analgesic to achieve a given reduction in pain; (5) an increase in duration of analgesic effect for a given dose of analgesic; (6) cumulative or lasting reduction of pain; and (7) an increase in the overall perceived efficacy of analgesic, such as a reduction in pain intensity experienced by the patient or other subjective or objective measures of efficacy disclosed herein.

Although favorable outcomes might be understood as a quantifiable reduction in the amount of analgesia required to achieve a given pain reduction and/or a quantifiable reduction in pain for a given amount of analgesia received by the patient, other favorable outcomes can involve improvements in the effectiveness of VRNT or other artificial sensory experiences, such as in their ability to permit the patient to be less emotionally affected by the pain or to reinterpret the pain to lessen the perception of severity even if the actual level of pain intensity remains the same.

Therefore, favorable outcomes that can be provided by combinatorial therapy as disclosed herein include improved efficacy of VRNT or other artificial sensory experience as measured by one or more of: (1) an increase in the number of patients responding favorably to VRNT or other artificial sensory experience or responding to a greater extent to VRNT or artificial sensory experience; (2) a reduction in the number of therapy sessions before initial beneficial effects and/or cumulative effects are experienced; (3) shorter session durations required to yield desired or meaningful results; (4) a lower frequency of sessions needed to reach desired or meaningful results; (5) an increase in the duration of the beneficial effects of VRNT or other artificial sensory experience; (6) cumulative or lasting reduction of pain; and (7) an increase in the effectiveness of VRNT or other artificial sensory experience, such as a reduction in pain intensity experienced by the patient or other measures of effective disclosed herein.

A. Clinical Study 1: Combinatorial Treatment Vs Analgesia Control

A group of 50 patients suffering from pre-existing chronic pain, some of whom have already begun taking analgesics such as opioids and/or SRNIs to manage their pain, are given analgesics alone over a defined period of time to provide baseline analgesia control data. After the analgesia control period, the patients are given combinatorial therapy, including artificial sensory experience (VNRT) and analgesics, over a defined period of time and the results are tabulated. During both the analgesia control period and the combinatorial therapy period, the following results over time are obtained by periodically surveying the patients and tabulated: (i) whether and how much the patients are responding to the analgesic, (ii) time between taking analgesic and onset of pain reduction over time, (iii) dosage of analgesic, (iv) frequency of administration of analgesic, (v) duration of analgesic effect for a given dose, (vi) cumulative or lasting reduction of pain; and (vii) overall effectiveness of analgesia, such as reduction in pain intensity, decrease in negative emotions, increase in positive outlook on life, and other measures.

Comparative Example 1—Analgesia Control

The 50 patients with chronic pain are prescribed and administered an analgesic designed to reduce chronic pain for 30 days, which is the analgesia control period. With the understanding that the patients likely have different conditions causing chronic pain, different pain levels, are given different types and/or dosages of analgesics, and have different physiologies, psychologies, ages, and external circumstances, the experience of each patient taking an analgesic is nonetheless the baseline for that patient. Measures of improvement include a reduction of pain and/or analgesic usage while some involve an increase in efficacy of the analgesia and increased overall well-being of the patient. For purposes of quantifying the results and measuring the cumulative experience of all patients without changes in numeric scores of different metrics offsetting each other, a higher score for each metric will correlate with a more negative outcome and a lower score will correlate with a more positive outcome. Based on that assumption, on a scale of 1 to 10, with 1 being the best outcome and 10 being the worst outcome, a baseline score of 7 is assigned to each patient for each of the seven metrics, which means the cumulative baseline score for all 50 patients is 350 for each of the seven metrics, as shown in Table 1.

TABLE 1

| Metric | Cumulative Baseline Score For Analgesia Control |
| --- | --- |
| Patients responding to analgesics and/or extent of patient response to analgesics | 350 |
| Amount of time required for analgesic to take effect | 350 |
| Dosage or amount of analgesic required for a given pain reduction | 350 |
| Frequency of administration of analgesic to achieve a given reduction in pain | 350 |
| Duration of analgesic effect for a given dose of analgesic | 350 |
| Cumulative or lasting reduction of pain | 350 |
| Overall perceived efficacy of analgesic (e.g., reduction in pain intensity or other subjective or objective measures of efficacy) | 350 |

Example 2—Combinatorial Therapy of VRNT and Analgesia

The same 50 patients in the analgesia control are administered combinatorial therapy involving artificial sensory experience (VRNT) and the analgesic(s) prescribed and received by the patients during the analgesia control period. Although the patients likely have different conditions causing chronic pain, different pain levels, are given different types and/or dosages of analgesics, and have different physiologies, psychologies, ages, and external circumstances, the subjective experience of each patient during the combinatorial therapy period is compared to that same patient's experience during the analgesia control period and given a score for each of the seven metrics. Any improvement by a patient for a given metric can be quantified by a score between 1-6, with 6 being the smallest improvement and 1 being the greatest improvement. A score of 7 means no improvement, and a score between 8-10 means a worse outcome. The scores for all 50 of the patients in the study are added together to give a cumulative score, as shown in Table 2, which provides a statistically relevant comparison of the group experience as a whole during the combinatorial therapy period compared to the analgesia control period. While combinatorial therapy is not expected to provide a worse outcome than analgesia alone, there may be outliers who experience more pain or other worse outcomes due to external circumstances (e.g., deteriorating health, other injury, sickness, emotionally traumatic event, negative reactions to selected VRNT regimen, and the like).

TABLE 2

| Metric | Cumulative Combinatorial Therapy Score |
| --- | --- |
| Patients responding to analgesics and/or extent of patient response to analgesics | 290 |
| Amount of time required for analgesic to take effect | 250 |
| Dosage or amount of analgesic required for a given pain reduction | 200 |
| Frequency of administration of analgesic to achieve a given reduction in pain | 220 |
| Duration of analgesic effect for a given dose of analgesic | 170 |
| Cumulative or lasting reduction of pain | 190 |
| Overall perceived efficacy of analgesic (e.g., reduction in pain intensity or other subjective or objective measures of efficacy) | 200 |

As shown by the cumulative scores in Table 2, combinatorial therapy provides a net increase in positive outcomes for the group of 50 patients as a whole. Even if a subset of patients experience either no benefit or a worse outcome in one or more metrics, the cumulative scores show that the group as a whole experienced a net increase in beneficial outcomes in each metric or category when given combinatorial therapy compared to analgesia alone.

B. Clinical Study 2: Combinatorial Treatment Vs VRNT Control

A different group of 50 patients suffering from pre-existing chronic pain, some of whom have already begun using artificial sensory experience (VRNT) or analgesics to manage their pain, are provided with VRNT alone over a defined period of time to provide baseline VRNT control data. After the VRNT control period, the patients are given combinatorial therapy, including VNRT and analgesics, over a defined period of time and the results are tabulated. During both the VRNT control period and the combinatorial therapy period, the following results over time are obtained by periodically surveying the patients and tabulated: (i) whether and how much the patients are responding to VRNT, (ii) number of VRNT sessions before initial beneficial effects and/or cumulative effects are experienced, (iii) duration of VRNT sessions required to yield desired or meaningful results, (iv) frequency of VRNT sessions needed to reach desired or meaningful results, (v) duration of beneficial effects following VRNT sessions, (vi) cumulative or lasting reduction of pain; and (vii) overall effectiveness of VRNT, such as reduction in pain intensity, decrease in negative emotions, increase in positive outlook on life, and other measures.

Comparative Example 3—VRNT Control

The 50 patients with chronic pain are prescribed and administered a VRNT regimen to address or mitigate chronic pain for 30 days, which is the VRNT control period. With the understanding that the patients likely have different conditions causing chronic pain, different pain levels, might respond differently to VRNT, and have different physiologies, psychologies, ages, and external circumstances, the experience of each patient receiving VRNT is nonetheless the baseline for that patient. Measures of improvement include a reduction of pain and/or number of VRNT sessions and/or session duration while some involve an increase in efficacy of VRNT and increased overall well-being of the patient. For purposes of quantifying the results and measuring the cumulative experience of all patients without changes in numeric scores of different metrics offsetting each other, a higher score for each metric will correlate with a more negative outcome and a lower score will correlate with a more positive outcome. Based on that assumption, on a scale of 1 to 10, with 1 being the best outcome and 10 being the worst outcome, a baseline score of 7 is assigned to each patient for each of the seven metrics, which means the cumulative baseline score for all 50 patients is 350 for each of the seven metrics, as shown in Table 3.

TABLE 3

| Metric | Cumulative Baseline Score For VRNT Control |
| --- | --- |
| Patients responding to VRNT and/or extent of patient response to VRNT | 350 |
| Number of sessions of VRNT before initial beneficial or cumulative effects of VRNT are experienced | 350 |
| Duration of VRNT sessions required for a given reduction in pain or other beneficial result | 350 |
| Frequency of VRNT sessions needed to reach a given reduction in pain or other beneficial result | 350 |
| Duration of beneficial effects following VRNT sessions | 350 |
| Cumulative or lasting reduction of pain | 350 |
| Overall perceived efficacy of VRNT (e.g., reduction in pain intensity or other subjective or objective measures of efficacy) | 350 |

Example 4—Combinatorial Therapy of VRNT and Analgesia

The same 50 patients in the VRNT control are administered combinatorial therapy involving VRNT as received during the VRNT control period and an analgesic appropriate for the type of chronic pain experienced by each patient. Although the patients likely have different conditions causing chronic pain, different pain levels, might respond differently to VRNT, and have different physiologies, psychologies, ages, and external circumstances, the subjective experience of each patient during the combinatorial therapy period is compared to that same patient's experience during the VRNT control period and given a score for each of the seven metrics. Any improvement by a patient for a given metric can be quantified by a score between 1-6, with 6 being the smallest improvement and 1 being the greatest improvement. A score of 7 means no improvement, and a score between 8-10 means a worse outcome. The scores for all 50 of the patients in the study are added together to give a cumulative score, as shown in Table 4, which provides a statistically relevant comparison of the group experience as a whole during the combinatorial therapy period compared to the VRNT control period. While combinatorial therapy is not expected to provide a worse outcome than analgesia alone, there may be outliers who experience more pain or other worse outcome due to external circumstances (e.g., deteriorating health, other injury, sickness, emotionally traumatic event, negative reactions to the selected analgesic, and the like).

TABLE 4

| Metric | Cumulative Combinatorial Therapy Score |
| --- | --- |
| Patients responding to VRNT and/or extent of patient response to VRNT | 270 |
| Number of sessions of VRNT before initial beneficial or cumulative effects of VRNT are experienced | 230 |
| Duration of VRNT sessions required for a given reduction in pain or other beneficial result | 180 |
| Frequency of VRNT sessions needed to reach a given reduction in pain or other beneficial result | 200 |
| Duration of beneficial effects following VRNT sessions | 150 |
| Cumulative or lasting reduction of pain | 170 |
| Overall perceived efficacy of VRNT (e.g., reduction in pain intensity or other subjective or objective measures of efficacy) | 190 |

As shown by the cumulative scores in Table 4, combinatorial therapy provides a net increase in positive outcomes for the group of 50 patients as a whole. Even if a subset of patients experience either no benefit or a worse outcome in one or more metrics, the cumulative scores show that the group as a whole experienced a net increase in beneficial outcomes in each metric or category when given combinatorial therapy compared to VRNT alone.

Example 5

Figure 2:
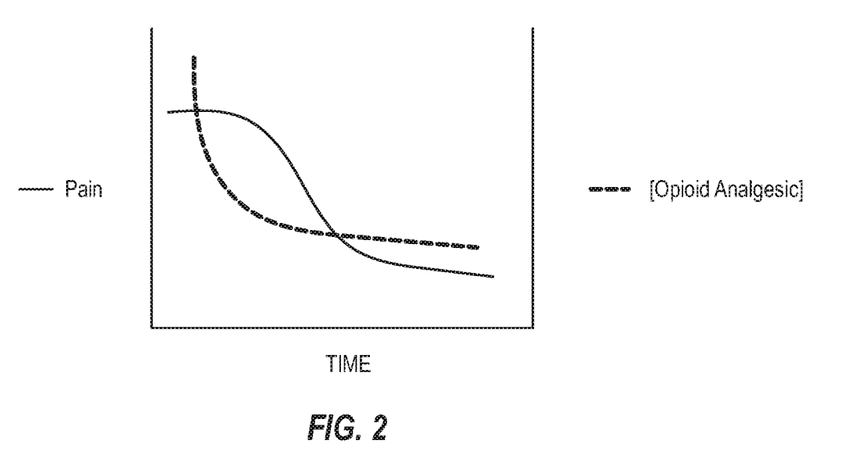
FIG. 2 illustrates an exemplary graph of a patient's pain over time with respect to the concentration of opioid analgesic over time that is administered in a combinatorial therapeutic according to the present disclosure.

Referring now to FIG. 2, which is a graph illustrating an amount or perceived amount of pain over time (represented by the solid line) and a concentration of opioid analgesic (represented as the broken line) over time that is used in a combinatorial therapeutic system/method in accordance with the present disclosure. As shown in the exemplary graph, one or both of the (perceived) pain level and opioid concentration decrease over time. At the first point in time on the graph, the patient may be at a prescribed (e.g., clinically relevant) level of opioid that has reached an equilibrium or steady state level of pain such that the opioid analgesic is having no better pain-relieving effects by itself. However, when coupled with an artificial sensory experience (e.g., VRNT), the administered concentration of opioid analgesic rapidly decreases to a lesser concentration. The reduced concentration of opioid analgesic maintains the same level of (perceived or actual) pain in the patient at first, followed by a decrease in the patient's (perceived or actual) pain. In some embodiments, there is a delayed reduction of pain (as shown), but it should be appreciated that in some embodiments, the opioid analgesic concentration can remain constant with a drop in the level of (perceived or actual) pain. Accordingly, as shown in FIG. 1, a combinatorial therapeutic system/method including an opioid analgesic and artificial sensory experience can demonstrate a synergistically beneficial relationship.

It should be appreciated that although FIG. 2 illustrates the concentration of opioid analgesic as decreasing rapidly to a second steady state concentration, other reaction modalities are possible. For example, the opioid analgesic concentration may decrease linearly over time or may have multiple asymptotic thresholds. Similarly, the amount of perceived pain may have a different distribution or affect in response to the combinatorial therapy. The pain may decrease and increase cyclically with or without a trend of decreasing pain over time. The pain may decrease only insofar as the combinatorial therapy is being received or it may decrease in correlation with the amount of time (per session or longitudinally) the combinatorial therapy is administered. Regardless, the combinatorial therapy of an opioid analgesic and an artificial sensory experience such as VRNT results in greater efficacy of the opioid analgesic, greater efficacy of VRNT, and/or reduces the amount of pain experienced by the patient at a same level of opioid analgesic and/or amount of VRNT.

Example 6

Figure 3:
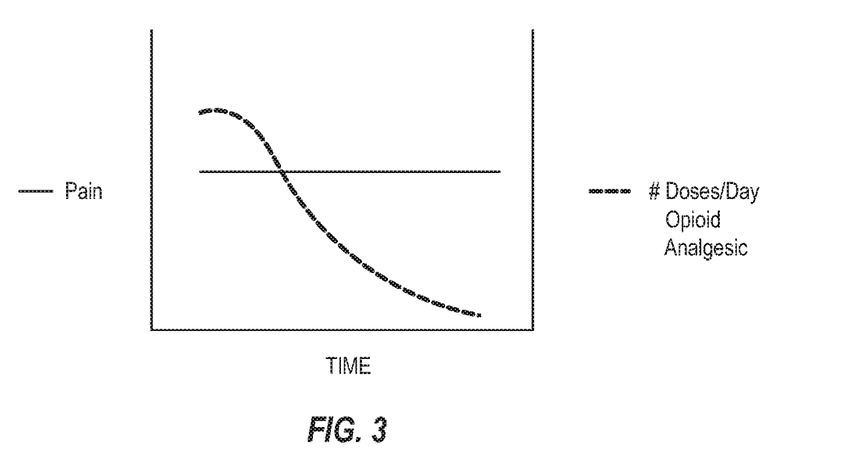
FIG. 3 illustrates an exemplary graph of a patient's pain over time with respect to the number of doses per day of an opioid analgesic over time that is administered in a combinatorial therapeutic according to the present disclosure.

As shown in FIG. 3, if the amount of pain (represented by the solid line of FIG. 3) is maintained (e.g., at or below a comfortable or acceptable level), the synergistic relation displayed by combinatorial therapeutic systems/methods disclosed herein can enable a decrease in the number of doses of opioid analgesic taken per day and/or amount of VRNT required. It will be appreciated that opioid usage can also be represented as a measure of the amount of daily equivalent doses of opioid analgesic (represented by the broken line of FIG. 3). Similarly, the dosage amount can decrease in some embodiments. Additionally, or alternatively, the number of doses per day of opioid analgesic can remain constant with a concomitant decrease in the amount of pain (not shown) and/or concomitant decrease in VRNT.

Examples 7-8

Figure 4A:
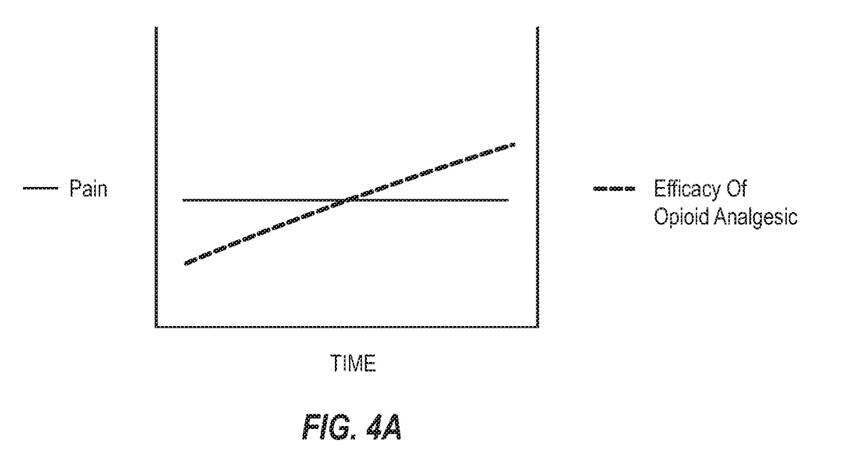
FIG. 4A illustrates an exemplary graph of a patient's pain over time with respect to the efficacy of an opioid analgesic, as included within a combinatorial therapeutic according to the present disclosure.
Figure 4B:
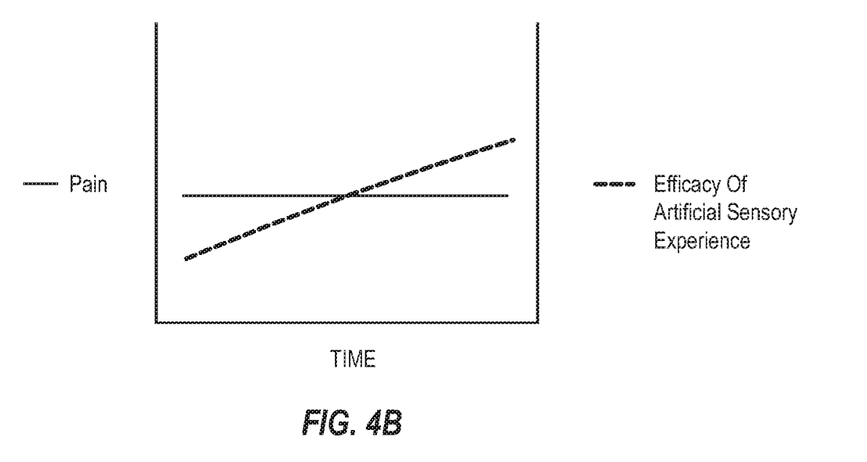
FIG. 4B illustrates an exemplary graph of a patient's pain over time with respect to the efficacy of an artificial sensory experience over time, as included within a combinatorial therapeutic according to the present disclosure.

As shown in FIG. 4A, combinatorial therapeutic systems/methods disclosed herein can increase the efficacy of the opioid analgesic over time while maintaining (or in some instances reducing) the amount of pain experienced by the patient. As shown in FIG. 4B, combinatorial therapeutic systems/methods disclosed herein can increase the efficacy of the artificial sensory experience (e.g., VRNT) over time while maintaining (or in some instances reducing) the amount of pain experienced by the patient. It should be appreciated that the synergistic benefits of combining an artificial sensory experience with an opioid analgesic described throughout the present disclosure, can cause an increase in the efficacy of the opioid analgesic (FIG. 4A) and/or of VRNT (FIG. 4B), and this increase in efficacy can result in a reduced prescription concentration (e.g., FIG. 2) or number of doses (e.g., FIG. 3) of the opioid analgesic. In some instances, it may additionally reduce the amount and/or number of times the artificial sensory experience is engaged by the user.

Example 9

In one embodiment, the combinatorial system may be combined with an analgesic mechanism (e.g., opioid drip, etc.), which controls the amount of opioid analgesic being delivered to the subject. Measuring the amount of opioid analgesic the subject uses may be used to break or reduce addictions or otherwise limit the total amount of opioid analgesics received by and/or available to the population at large. In still another embodiment, the system may be combined with one or more biofeedback devices (e.g., heart rate/heart rate variability monitor, galvanic skin response monitor, electroencephalogram/EEG, fMRI, etc.) which may, for example, provide other data to evaluate patient pain levels or other patient data.

Examples 10-12

Figure 5A:
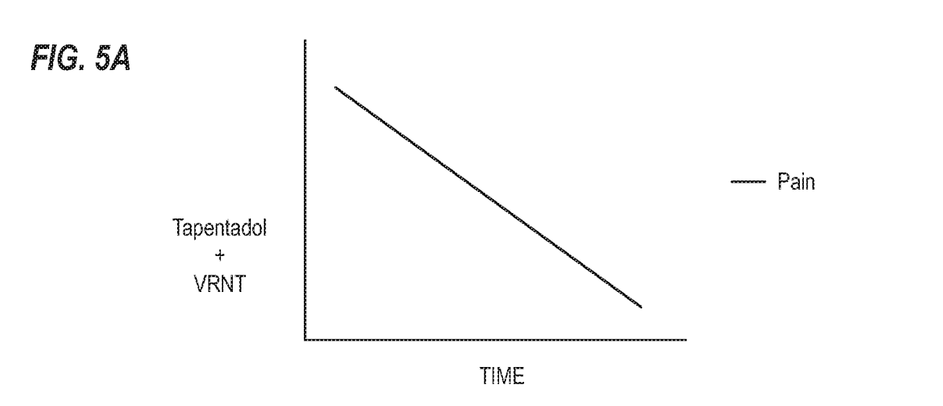
FIGS. 5A-5C illustrate exemplary graphs of potential effects of combinatorial therapeutic systems/methods employing tapentadol and VRNT on a patient's amount of pain over time.
Figure 5B:
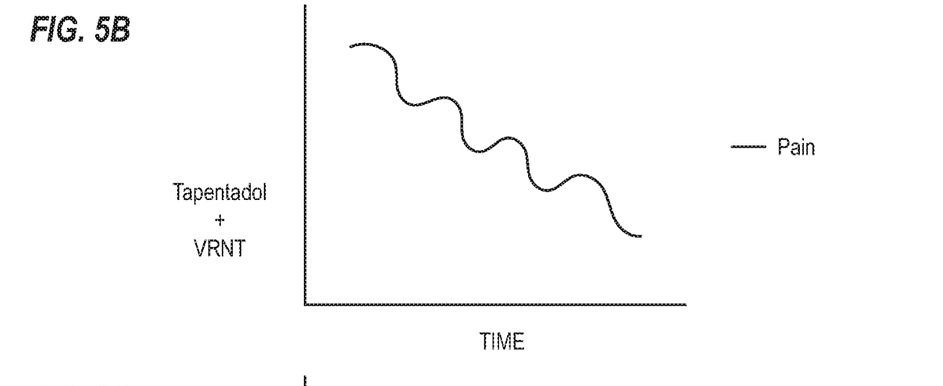
Figure 5C:
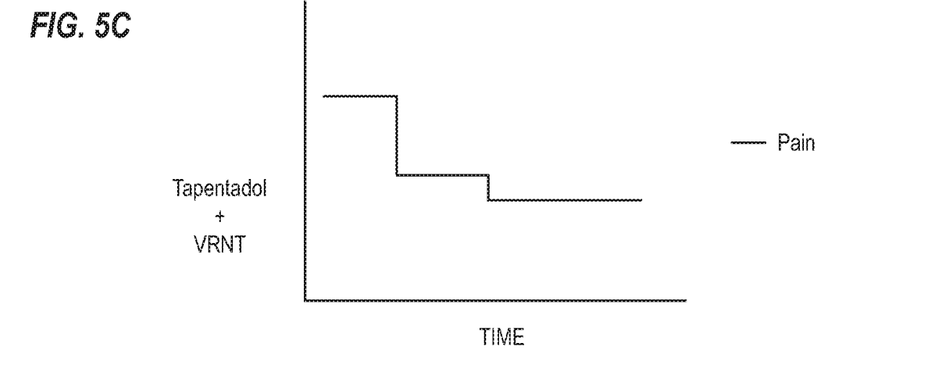

The synergistic effects of the disclosed combinatorial therapeutic systems/methods can be exemplified in a plurality of responses. For example, FIGS. 5A-5C illustrate a combinatorial therapy using tapentadol (as the opioid analgesic) and VRNT (as the artificial sensory experience) with different potential patient responses. As many, if not all, patients may experience the synergistic benefits afforded by the disclosed combinatorial therapeutic systems/methods as an average benefit, the individual-specific responses may be different.

For example, as shown in FIG. 5A (Example 10), a patient using a combinatorial therapeutic system with tapentadol and VRNT may experience a constant or linear decrease in pain over time. Some patients may experience a different response.

As shown in FIG. 5B (Example 10), a patient using a combinatorial therapeutic system with tapentadol and VRNT may experience a cyclical decrease and increase in pain levels over time with an overall decreasing pain level from a first time point to a second, later time point.

As an additional example (Example 12), a patient using a combinatorial therapeutic system with tapentadol and VRNT may experience a step-wise reduction in pain levels, as shown in FIG. 5C.

Example 13

It should be appreciated that although FIGS. 5A-5C illustrate examples of a combinatorial therapeutic system/method with tapentadol and VRNT, the same or similar results should be expected for opioid analgesics oxycodone, cepranopradol, difelikefalin (CR845), and a combination of oxycodone and acetaminophen (e.g., Percocet®). Similarly, although VRNT is shown as the exemplary artificial sensory experience, the same or similar results may be expected for other artificial sensory experiences disclosed herein (e.g., 2D/3D/4D artificial sensory experiences, holography systems, other virtual reality systems, augmented reality systems, and/or mixed reality systems.)

It should be further appreciated that different patients may respond differently to the combinatorial therapy and may demonstrate a mixture of responses shown in FIGS. 5A-5C—or other responses. However, a significant proportion of patients utilizing the combinatorial systems/methods disclosed herein as intended will demonstrate an overall decrease in an amount or frequency of pain and/or longer lasting analgesic effect and may, in some instances, cause a patient to no longer experience chronic pain and/or eliminate a patient's symptomatic pain.

Examples 14-15

Figure 6A:
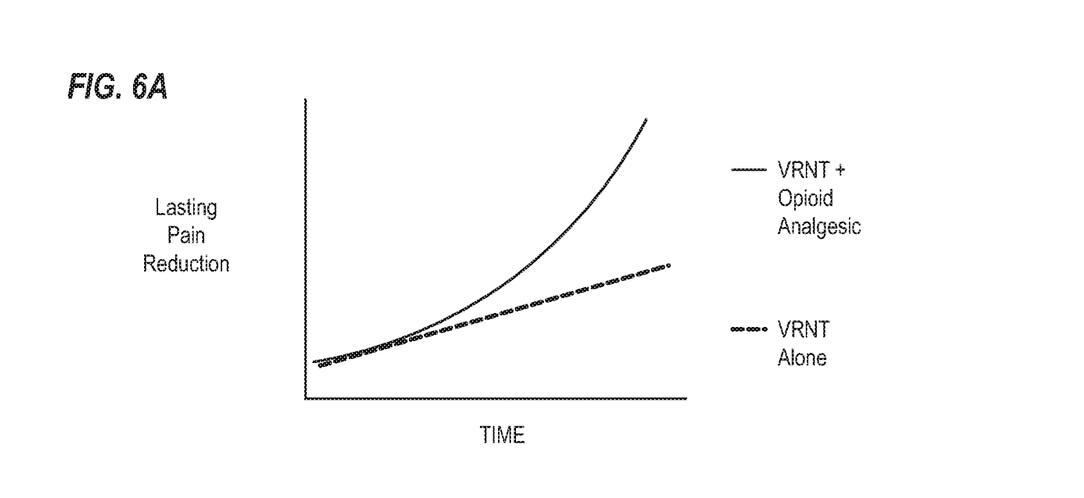
FIGS. 6A and 6B illustrate exemplary graphs of potential effects of combinatorial therapeutic systems/methods employing an opioid analgesic and VRNT on a patient's response to VRNT.
Figure 6B:
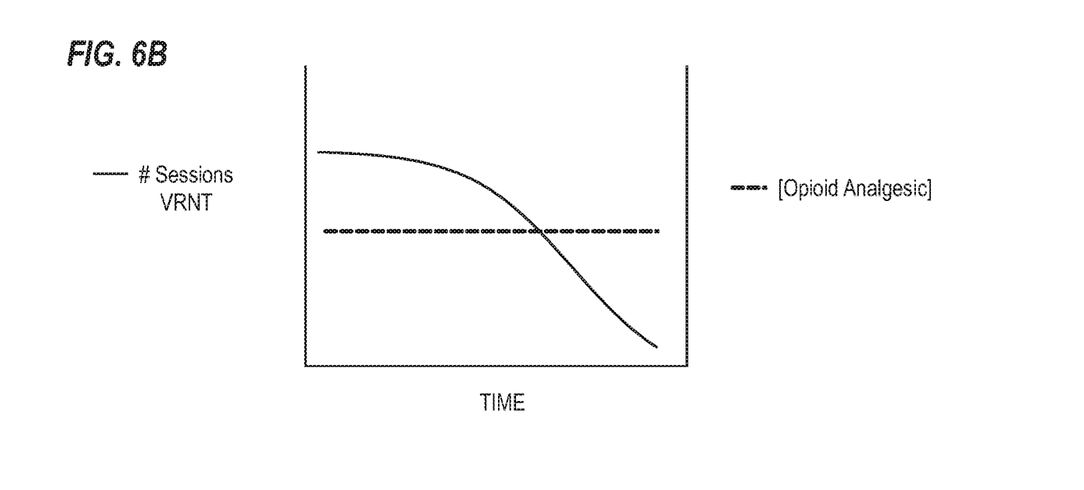

In some embodiments, the combinatorial therapeutic systems/methods may increase the effectiveness of the artificial sensory experience. For example, as shown in FIGS. 6A and 6B, an opioid analgesic—when used in combination with an artificial sensory experience such as VRNT—can accelerate or increase lasting pain reduction (FIG. 6A) and/or reduce the number of trainings/sessions with the artificial sensory experience to achieve a beneficial reduction in pain (FIG. 6B). It should be appreciated that although FIGS. 6A and 6B illustrate the effects of combinatorial therapy using VRNT, other artificial sensory experiences may demonstrate the same or similar benefits. Without being bound to a particular theory, the results shown in FIGS. 6A and 6B may theoretically occur because the patient feels less pain while practicing VRNT and/or the opioid analgesic can provide a beneficial amelioration of pain that is being visualized during VRNT. This may provide positive reinforcement to the psyche and/or willpower of the patient over their pain (e.g., the patient believes they are in control or can control the pain instead of being subject to it).

SNRIs and Pain Management

As provided above, opioid-based pharmaceuticals are effective analgesics and when coupled with an artificial sensory experience (as described herein), the salubrious analgesic effects can be unexpectedly increased. That is to say, the combinatorial therapeutic systems and methods described thus far have focused on combinations of opioid analgesics with an artificial sensory experience to treat and/or mitigate pain, especially chronic or recurrent pain. It should be appreciated, however, that similar salubrious effects may be observed in other conditions.

For example, the foregoing systems may prove beneficial in the treatment of fibromyalgia. In some embodiments, however, the concepts described above can be applied to a fibromyalgia-specific combinatorial therapeutic system and/or treatment method. Such an exemplary combinatorial therapeutic system could provide a synergistic improvement to efficacy of pharmaceuticals prescribed to treat fibromyalgia by, for example, decreasing the concentration of said pharmaceuticals that can be administered for analgesic effect (similar to that shown and described in FIG. 2), decreasing the average daily dose of said pharmaceuticals that is administered to maintain a particular perceived pain level (similar to that shown and described in FIG. 3), increasing the efficacy of said pharmaceuticals administered to maintain a particular perceived pain level (similar to that shown and described in FIG. 4A), and/or increasing the efficacy of the artificial sensory experience (e.g., VRNT) to maintain a particular perceived pain level (similar to that shown and described in FIG. 4B).

Example 16

In an exemplary embodiment, a combinatorial therapeutic system for treating fibromyalgia includes a serotonin-norepinephrine reuptake inhibitor (SNRI) and an artificial sensory experience. The SNRI can include milnacipran, specifically, and in some embodiments, the SNRI can include other SNRIs commonly prescribed to treat fibromyalgia (e.g., duloxetine). Similar to those combinatorial systems described above, the artificial sensory experience combined with the SNRI (preferably milnacipran) can include any of 2D/3D/4D artificial sensory experiences, holography, augmented reality, virtual reality, and/or mixed reality. In an exemplary embodiment, the artificial sensory experience is VRNT or virtual reality distraction therapy.

Methods for treating/mitigating pain associated with fibromyalgia can include receiving a combinatorial therapeutic system, as described above.

In some embodiments, the combinatorial treatment systems and methods for treating/mitigating pain associated with fibromyalgia can have similar results to those illustrated and described with respect to FIGS. 5A, 5B, 5C, 6A, and 6B. That is, combinatorial treatment systems that include milnacipran and VRNT or virtual reality distraction therapy can cause a decrease in pain over time (e.g., as a linear decrease over time similar to that shown in FIG. 5A, as a sinusoidal trending decrease over time similar to that shown in FIG. 5B, or a stepwise decrease over time similar to that shown in FIG. 5C).

Further, in some embodiments, the combinatorial therapeutic systems/methods for treating/mitigating pain associated with fibromyalgia may increase the effectiveness of the artificial sensory experience. For example, combination therapeutic systems/methods that include milnacipran (or other SNRI used to treat fibromyalgia) in combination with an artificial sensory experience such as VRNT or virtual reality distraction therapy can accelerate lasting pain reduction (similar to that shown in FIG. 6A) and/or reduce the number of trainings/sessions with the artificial sensory experience to achieve a beneficial reduction in pain (similar to that shown in FIG. 6B). Without being bound to a particular theory, the combined use of SNRIs and an artificial sensory experience may provide positive reinforcement to the psyche and/or willpower of the patient over their pain (e.g., the patient believes they are in control or can control the pain associated with fibromyalgia instead of being subject to it).

Pain Symptoms, Emotions, Quality of Life, and Effects

While the description of combinatorial therapies focuses on patients' experience of pain, it will be appreciated that what constitutes "pain" can be manifest, experienced, or understood in different ways by different patients and/or by the same patient at different times. Examples of ways to understand the mean of pain include pain intensity, frequency of (severe) pain episodes, severity of pain episodes, secondary pain effects, such as emotional suffering, stress, depression, fear or anxiety, quality of life, mobility, movement, activity limitations, disability (level of), kinesiophobia (fear of movement), areas of body in pain, cessation of expansion of pain or deterioration of pain symptoms, predictability of pain, sense of "normal" body sensations, sense of self-efficacy (or sense of helplessness), overall satisfaction with treatment(s), life orientation, pain catastrophying, anger regulation, pain attitude, pain coping, avoidance of surgery, and the like. Each of these can be used as outcome measures to measure the effectiveness of a therapy.

Example Mechanisms of Synergy—Analgesics Assisting VRNT

Analgesics can assist VRNT, which seeks to train the brain pain control mechanisms. Analgesics give patients relief and the brain interprets this as validation of increased pain control, self-efficacy, and the like, leading to faster psychological acceptance and more lasting neuroplastic change.

VRNT uses psychological tools such as self-distancing and separation of physical and psychological experience. Analgesics give patients short-term relief and thus the ability to focus on the psychological tasks, leading to faster psychological acceptance and more lasting neuroplastic change.

VRNT uses exposure therapy tools to lessen the feelings of threat. Analgesics reduce pain intensity, allowing patients to feel temporary reduction in threat, while doing VRNT, leading to faster psychological acceptance and more lasting neuroplastic change.

VRNT requires relaxation and mind-body connection and deep psychological engagement in the psychological training. Analgesics can pause the overriding psychological disruption caused by severe pain. Alternatively, or in addition, it can be a relaxant and can numb other mind-chatter, which can lead to substantively increased mind-body connection and patients' ability to engage in the psychological training.

Example Mechanisms of Synergy—VRNT Assisting Analgesics

Centrally acting analgesics can rely on psychological state (and placebo effect) for efficacy. VRNT increases the patients' own pain control, their feeling of self-efficacy, and their sense of optimism about pain outcomes, and reduces fear of pain, increasing the analgesic effectiveness of the analgesic and/or psychological perception thereof.

Centrally acting analgesic can provide pain relief or perception thereof. VRNT can be designed to create an audio-visual (plus tactile or other sensory) environment that mimics the effects of the analgesic. It could also exaggerate or accelerate these effects, which can lead the brain to believe in a much more powerful analgesic effect than the analgesic provides, leading to higher responder rates (more people responding to opioids) and/or greater levels of analgesic effects.

Accordingly, methods and systems are provided for treating pain. The concepts and features described herein may be embodied in other specific forms without departing from their spirit or descriptive characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

The invention claimed is:

1. A combinatorial therapeutic system for treating and/or mitigating pain, comprising:
   a therapeutically effective amount of an analgesic selected from tapentadol or difelikefalin (CR845); and
   a computer system that includes at least one processor, computer-readable memory, and an output device, the computer system configured to provide an artificial sensory experience comprising one or more of a 2D artificial sensory experience, a 3D artificial sensory experience, a 4D artificial sensory experience, holography, augmented reality, virtual reality, or mixed reality,
   wherein the output device is configured to produce, during the artificial sensory experience, sensory stimuli comprising a virtual representation of a patient's symptom that is perceptible to the patient, wherein the symptom includes pain, and
   wherein the computer system is configured to cause the virtual representation of the patient's pain to perceptibly change during the artificial sensory experience.

2. The combinatorial therapeutic system of claim 1, wherein the artificial sensory experience comprises virtual reality neuropsychological therapy (VRNT).

3. The combinatorial therapeutic system of claim 1, wherein the artificial sensory experience comprises a 4D artificial sensory experience that is implemented as a 3D visual stimulus within virtual reality, augmented reality, or mixed reality and at least one additional sensory stimulus selected from a tactile stimulus, an auditory stimulus, an olfactory stimulus, and a gustatory stimulus.

4. The combinatorial therapeutic system of claim 1, further comprising a 3D sensory experience that is implemented as (i) a 3D visual stimulus or (ii) as a combination of a 2D visual stimulus and at least one additional sensory stimulus selected from a tactile stimulus, an auditory stimulus, an olfactory stimulus, and a gustatory stimulus.

5. The combinatorial therapeutic system of claim 1, wherein the virtual representation of the patient's pain comprises one or more of a visual, auditory, tactile, olfactory, or gustatory representation of the pain associated with an avatar representative of the patient.

6. The combinatorial therapeutic system of claim 5, wherein the virtual representation of the patient's pain comprises a visual indicator of the pain displayed on the avatar of the patient.

7. The combinatorial therapeutic system of claim 6, wherein the visual indicator of the pain displayed on the avatar representative of the patient is variable in one or more of location, color, or intensity.

8. The combinatorial therapeutic system of claim 1, wherein the perceptible change in the virtual representation of the patient's pain comprises a virtual representation of alleviation of the patient's pain.

9. The combinatorial therapeutic system of claim 8, wherein the perceptible change in the virtual representation of the patient's pain comprises a perceptible change in one or more of a visual, auditory, tactile, olfactory, or gustatory representation of the patient's pain.

10. The combinatorial therapeutic system of claim 1, wherein the computer system is configured to generate the virtual representation of the patient's pain based at least in part on user input received by the computer system via an input device.

11. A method for treating and/or mitigating pain in a patient by providing a combinatorial therapy, the method comprising:
   providing a therapeutic dose of an analgesic selected from tapentadol or difelikefalin (CR845); and
   providing an artificial sensory experience by way of a computer system that includes at least one processor and computer-readable memory, the artificial sensory experience comprising one or more of: a 2D artificial sensory experience, a 3D artificial sensory experience, a 4D artificial sensory experience, holography, augmented reality, virtual reality, or mixed reality,
   wherein the artificial sensory experience provides sensory stimuli to the patient, the sensory stimuli comprising a virtual representation of the patient's symptom that is perceptible to the patient, and
   wherein the virtual representation of the patient's symptom undergoes a perceptible change during the artificial sensory experience.

12. The method of claim 11, wherein receiving an artificial sensory experience comprises receiving virtual reality neuropsychological therapy (VRNT).

13. The method of claim 12, wherein receiving the therapeutic dose of the analgesic and receiving VRNT results in a synergistic interaction to reduce one or more of analgesic usage or a number or duration of VRNT sessions for treating and/or mitigating the pain.

14. The method of claim 13, wherein receiving the artificial sensory experience comprises receiving a 4D artificial sensory experience, the method further comprising receiving a 3D sensory experience separate from the 4D artificial sensory experience, the 3D sensory experience selected from: (i) a 3D visual stimulus or (ii) a 2D visual stimulus and at least one additional sensory stimulus selected from an additional tactile stimulus, an additional auditory stimulus, an additional olfactory stimulus, and an additional gustatory stimulus.

15. The method of claim 13, wherein receiving the artificial sensory experience comprises receiving a 4D artificial sensory experience, the method further comprising receiving a 2D visual stimulus separate from the 4D artificial sensory experience, wherein receiving the 2D visual stimulus maintains the reduction in the analgesic usage or in the number or duration of VRNT sessions for treating and/or mitigating the pain.

16. The method of claim 11, wherein receiving the artificial sensory experience comprises receiving a 4D sensory experience that is implemented as a 3D visual stimulus and at least one additional sensory stimulus selected from a tactile stimulus, an auditory stimulus, an olfactory stimulus, and a gustatory stimulus.

17. The method of claim 11, wherein the combinatorial therapy is provided to the patient over a combinatorial therapy period during which (i) one or more doses of the analgesic and (ii) one or more sessions of the artificial sensory experience are provided to the patient.

18. The method of claim 11, wherein the combinatorial therapy comprises administering a regimen of multiple doses of the analgesic and a regimen of multiple sessions of the artificial sensory experience during the therapy period.

19. A combinatorial therapeutic system for treating and/or mitigating pain, comprising:
 a therapeutically effective amount of an analgesic selected from tapentadol or difelikefalin (CR845); and
 a computer system that includes at least one processor, a computer-readable memory, and an output device, the computer system configured to provide an artificial sensory experience comprising one or more of a 2D artificial sensory experience, a 3D artificial sensory experience, a 4D artificial sensory experience, holography, augmented reality, virtual reality, or mixed reality,
 wherein the output device is configured to produce, during the artificial sensory experience, sensory stimuli comprising a virtual representation of a patient's symptom that is perceptible to the patient,
 wherein the computer system is configured to cause the virtual representation of the patient's symptom to perceptibly change during the artificial sensory experiences, and
 wherein the artificial sensory experience does not comprise distraction therapy.

20. The combinatorial therapeutic system of claim 19, wherein the system is configured for treating and/or mitigating chronic pain.

* * * * *